United States Patent [19]

Allain

[11] 3,959,391

[45] May 25, 1976

[54] DIETHERS OF POLYALKYLENE GLYCOL

[75] Inventor: Ronald J. Allain, Brookhaven, Miss.

[73] Assignee: Nalco Chemical Company, Oak Brook, Ill.

[22] Filed: Apr. 11, 1975

[21] Appl. No.: 567,326

Related U.S. Application Data

[63] Continuation-in-part of Ser. No. 346,220, March 29, 1973, abandoned.

[52] U.S. Cl. ........................ 260/615 B; 260/615 R
[51] Int. Cl.$^2$ .......................................... C07C 41/00
[58] Field of Search ................... 260/615 R, 615 B

[56] References Cited
UNITED STATES PATENTS

| | | | |
|---|---|---|---|
| 2,271,873 | 2/1942 | Perkins et al. | 260/615 R |
| 2,520,611 | 8/1950 | Roberts et al. | 260/615 B |
| 2,520,733 | 8/1950 | Morris et al. | 260/615 B |
| 2,575,298 | 11/1951 | Ryznar | 260/615 B X |
| 2,596,091 | 3/1952 | Benneville | 260/615 B |
| 2,919,293 | 12/1959 | Weisse | 260/615 R |

FOREIGN PATENTS OR APPLICATIONS

| | | | |
|---|---|---|---|
| 706,432 | 3/1915 | Canada | 260/615 B |
| 788,489 | 6/1968 | Canada | 260/615 R |

*Primary Examiner*—Howard T. Mars
*Attorney, Agent, or Firm*—John G. Premo; John S. Roberts

[57] ABSTRACT

A method of increasing the yield of diethers from polyethylene glycols utilizing sodium hydroxide and an alkyl halide as condensing reactants. A normal yield of 70–75% of the diether at the end point of the reaction may be increased to 95–99% by separating out the sodium chloride product and then adding in a supplemental reaction lesser incremental amounts of from 20–25% each (based upon theoretical) of sodium hydroxide and alkyl halide reactants together with elimination of water of reaction by a condensation trap or binary azeotropic distillation. The organic phase of the azeotropic pair is selected preferably from organics of the BTX series such as toluene, which reagents are free from functional groups which would interfere later with the use of the diether product as a Grignard reagent solvent in the Nalco Freeport Process for the production of organolead additives using a sacrificial lead anode. [Encyclopedia of Chemical Technology (ECT) II, Volume 12, Interscience, 1967, pages 292–293].

6 Claims, No Drawings

DIETHERS OF POLYALKYLENE GLYCOL

This is a continuation-in-part application of pending Ser. No. 346,220 now abandoned, filed Mar. 29, 1973, of Ronald J. Allain, entitled "Diethers of Polyalkylene Glycol."

The production of ethers, including the production of diethers of the present invention, generally dates back to Dr. A. W. Williamson, the developer of the so-called Williamson synthesis, which is described as the reaction of a sodium alkoxide with an alkyl halide to form an ether, 1850. The application of the Williamson synthesis to the present invention lies in a modification wherein alcohol and sodium hydroxide are utilized instead of an alkoxide or the sodium metal. One difficulty with the Williamson synthesis according to modern texts is in the yields. Fieser and Fieser, *Organic Chemistry*, 3d Edition, Reinhold, 1956, page 137, shows the production of ethyl n-propyl ether of 70%.

The reaction of the present invention may be graphically portrayed by the following equation showing a substitution reaction $$HO-(CH_2CH_2O)_n-CH_2CH_2OH + 2RX + 2NaOH \rightarrow$$
$$RO-(CH_2CH_2O)_n-CH_2CH_2OR + 2NaX + 2H_2O$$

$R = C_1-C_6$ alkyl
$X =$ halogen, preferably Cl
$n = 1-6$

Corroborating the literature, it has been found that in normal operation the commercial end point of the reaction is when the reaction has proceeded towards the right to about a 70% diether yield.

The patent art of interest is as follows:

U.S. Pat. No. 2,520,611 Roberts et al. — Column 4 of this patent indicates that excesses of organic halide in a main reaction may be utilized up to 8 moles of halide per mole of diol, which may be expressed as about 4:1 equivalents of the reactant and utilizing in addition 1.25 moles of sodium hydroxide (solid). At column 5, lines 5-11, water removal is noted but no utilization of separate supplemental reaction is mentioned where concurrently water is removed. Additionally, in the patent the time parameter for the reaction is given as 20-30 hours at column 5, line 12.

Canadian 788,489 – A process for tri-etherifying a monoalkyl ether of glycerol with excess alkyl halide (at least 2 equivalents) and concurrently removing water from the mixture. The time here is 14-20 hours and no provision is made for a supplemental reaction.

In the present reaction the so-called fingerprint process indicia include operating at a temperature between 100-130°C and at a pressure from atmospheric to about 50 psig. Hence, the preferred alcohols to be etherified are polyalkylene glycols having two OH groups. The theoretical molar amounts necessary for both the sodium hydroxide and alkyl halide are 2 moles each for each molar unit of glycol used as reactants. Additionally, in commercial usage it has been found that a 20% excess of both hydroxide and alkyl halide are used in order to assist the reaction. Despite the use of such an excess, the end point of the reaction is reached in 4–6 hours using incremental amounts of reactants and stabilizes at about 67–75% product for a diether. For example, in using as a reactaant tetraethylene glycol the product, which is the diethylether of tetraethylene glycol (DETEG) is produced in 67–78% yield.

According to the present invention, after separation of the aqueous sodium chloride layer product, a supplemental reaction of the same nature as the primary reaction is commenced by addition of 20-25% sodium hydroxide and alkyl halide reactants. The addition of the sodium hydroxide and alkyl halide reactants in the supplemental reaction has resulted in an appreciable gain in the diether product from about 70% to at least 95%, ranging from 92.5–99+%. It is quite important that concurrently with the supplemental reaction the water formation be removed either by a cold trap or azeotropic distillation as with a BTX solvent (benzene-toluene-xylene). This elimination of the so-called water of formation which continues during a supplemental reaction and the addition of smaller molar amounts of the reactants (about 20–25% based on theoretical) in a supplemental reaction following phase separation and removal of sodium chloride after the main reaction are believed to be responsible for the increased yield of this process. Although agitation and other parameters may affect total time, it is noted that in the Roberts patent above, a reaction time is given over 20–30 hours for normal yields, whereas in the present process the time element involves 4–6 hours for the main reaction and about a like amount for the supplemental reaction, which is substantially less then 20–30 hours of treatment time and thus makes possible a saving of time.

ALCOHOL STARTING MATERIAL

Most preferred reactants of the present invention are polyglycols and more specifically polyalkylene glycols, such as diethylene glycol, triethylene glycol, tetraethylene glycol, and dipropylene glycol. A most preferred product is the diethylether of tetraethylene glycol (DETEG). These polyalkylene glycols in conjunction with tetrahydrofuran are utilized as solvents for the Grignard reagent in the production of tetramethyllead and other organo lead compounds as noted in such patents as 3,312,605; 3,359,291; 3,380,899; 3,409,518 all to Braithwaite, assigned to Nalco Chemical Company. Other operable starting materials include glycerine, trimethylol propane, and 2,2'-thiodiethanol.

ALKYL HALIDE STARTING MATERIAL

Since the reaction introduces the alkyl substituent into the alcohol moiety and the desired substituent is a lower alkyl or $C_1-C_6$ group, it is necessary that such a group as methyl, ethyl, propyl, and butyl be utilized to effect the desired reaction. A reactant of choice is ethyl chloride, a liquid. In the main reaction of the present invention the alkyl halide is utilized in about 20% excess of theoretical and in the supplemental reaction, to drive the yield from 70–95%, the alkyl halide is utilized again in about 25% of theoretical based upon the original reaction.

SODIUM HYDROXIDE STARTING MATERIAL

Sodium hydroxide is preferably used in flake form in similar quantities to the utilization of alkyl halide. Twenty percent in excess of theoretical may be utilized in the main reaction and about 25% is utilized in the supplemental reaction to increase the yield of diether. It is possible to substitute potassium hydroxide in solid form but the cost of the potassium base is substantially above that of sodium base. With adequate agitation and stirring of the reaction mix, it is possible to utilize only a total of about 20–25% excess sodium hydroxide in the overall reaction.

REMOVAL OF WATER OF FORMATION

AT the commercial end point, which is about 70% completion in the case of the product DETEG and others, one key factor enabling the increase of yield is the removal of water of formation from the organic layer. After completion of the main reaction, the aqueous layer containing the sodium chloride product is removed, but additional assistance is necessary to remove the water of formation entrained in the organic layer with the product diether. This may be accomplished either by the utilization of a Diens-Stark condensation water trap or, better, the utilization of an azeotropic distillation with addition of an organic such as toluene or other BTX solvent, and this removal of water is continued in a supplemental reaction.

For later use in the electrolytic Nalco Freeport Process reactive groups would be contra indicated so a benzene toluene-xylene (BTX) type solvent is necessary, and the utilization of divergent solvents such as disclosed in U.S. Pat. No. 2,228,929 Reibnitz at page 1, column 2, lines 25–36, is not made. A most preferred solvent is toluene, which forms an azeotrope with water wherein the azeotrope contains only 20.2% toluene and azeotrope boiling point of 85°C.

SODIUM CHLORIDE PRODUCT

The salt product which is formed in the main reaction settles to the bottom of the reactor and necessitates vigorous agitation of the reaction mix in order that it may not substantially cover up and retard the effectiveness of the alkali sodium hydroxide reactant. This salt product which forms in the aqueous phase is removed preferably by dissolving the sodium chloride and separating the aqueous layer from the organic layer.

THE SUPPLEMENTAL REACTION

In the supplemental reaction 20–25% each (based on theoretical in the main reaction) of sodium hydroxide and the alkyl halide starting material are added to the reaction mixture from which the bulk of the sodium chloride product has been removed. The removal of the sodium chloriide product occurs by phase separation and separates in the aqueous phase. As soon as the sodium chloride product is removed, the water of formation from the main reaction is removed by assistance by water trap or azeotropic distillation as set out above. In the supplemental reaction, process indicia of temperature (105–135°C), time (4–8 hours), and pressure (1 atmosphere to about 50 psig) are similar to those used in the main reaction. The supplemental reaction operating with lesser quantities of reactants and continued removal of water has been found to materially increase the yield of the diether product.

OTHER PROCESS LIMITATIONS AND VARIABLES

It has been found that in carrying out the process, an atmoshpere which excludes oxygen is advantageous and such an atmosphere can be provided by closed container with a nitrogen or other inert gas blanket such as helium, argon, neon, etc.

EXAMPLE 1

2910 g. (15,0 moles) of tetraethylene glycol was charged to a two-gallon stainless steel reactor. To this was added at two-hour intervals, 300 g. (7.5 moles) portions of NaOH flakes and 486 g. (7.6 moles) portions of $C_2H_5Cl$. The mixture was heated at 120°–125°C throughout the reaction and continuous agitation was utilized in the reactor. The maximum pressure developed in any stage of the reaction was 40 psig. The following data shows some of the results obtained:

| Hrs. | Wt. of EtCl Added | Wt. of NaOH Added | Sample Analysis | | |
|---|---|---|---|---|---|
| | | | DETEG* | METEG+ | TEG⁺ |
| 0 | 486g (7.6m) | 300g (7.5m) | 5.7% | 42.0% | 52.3% |
| 2 | 486g (7.6m) | 300g (7.5m) | 22.7% | 55.0% | 22.3% |
| 4 | 486g (7.6m) | 300g (7.5m) | 44.1% | 48.9% | 7.1% |
| 6 | 486g (7.6m) | 300g (7.5m) | 67.0% | 32.5% | 0.5% |
| 8 | 486g (7.6m) | 300g (7.5m) | 78.0% | 22.0% | 0.0% |

*Diethylether of tetraethylene glycol
+Monoethylether of tetraethylene glycol
⁺Tetraethylene glycol The first four additions represent the theoretical amount of caustic required and a 0.4 mole excess of ethylchloride.

Upon removal of this mixture from the reactor, three separate phases were noted; an upper layer consisting of the organics, a middle layer (approx. 300 ml) containing 30% aqueous caustic and a lower layer comprised essentially of crystalline NaCl. The salt or sodium chloride in the aqueous layer was discarded.

The layers were separated and the organics were combined to the original organic layer. Approximately 1.5 liters of toluene was added to this organic mixture and this resulting mixture was charged to a glass flask. 180 milliliters of water was removed by azeotropic distillation. The surplus ethyl chloride remaining in the solution aided in the removal of $H_2O$. About 500 milliliters of toluene was also removed. Analysis showed the resulting organic layer contained less than 1% $H_2O$.

Thus, after the NaCl had been discarded in the primary reaction, in a supplemental reaction 160 g. (4.0 moles) of NaOH flakes was added and the mixture heated to 120°–125°C. 4.1 moles of ethyl chloride was bubbled into the mixture. A Diens-Stark trap was used to remove some of the water as it was formed. After two hours, three 40 g. portions (120 g., 3.0 moles) of NaOH was added at two-hour intervals and 3.1 moles of ethyl chloride was added continuously during this time. Only about 15 milliliters of $H_2O$ was removed. The analysis of this mixture two hours after final addition of NaOH showed 99.6% DETEG and 0.4% METEG.

The reaction slowed at the 70% DETEG point due to the lack of NaOH availability in the organic phase. It is noted that only a small amount of water was removed in the supplemental reaction and this is believed unnecessary towards the increase in yields showed by the present example.

EXAMPLE 2910 g. (15.0 moles) of tetraethylene glycol was charged to a two-gallon stainless steel reactor. 1200 g. (30.0 moles) of NaOH flakes and 1944 g. (30.4 moles) of ethyl chloride was added while maintaining the temperature at 105°C. The maximum pressure obtained was 40 psig. The NaOH and EtCl were added in 300 g. and 486 g. portions, respectively. The total time for these additions was 3.5 hours. After the additions were completed, the mixture was stirred overnight at 105°C. At this point g.c. analysis showed the mixture to be 67% DETEG, 32.7% METEG and 0.3% TEG.

Water was then added to dissolve the NaCl and the layers were separated. The organic layer and 1500 milliliters toluene were returned to the reactor. Water was azeotropically removed. 380 milliliters of water was removed in just under an hour. The presence of ethyl chloride is believed to enhance the rate at which water is removed.

In a supplemental reaction 200 g. (5.0 moles) of NaOH and 360 g. (5.6 moles) of ethyl chloride were added and this mixture stirred overnight at 105°C. Analysis showed 96.6% DETEG and 3.4% METEG. An additional 100 g. (2.5 moles) NaOH and 180 g. (2.8 moles) ethyl chloride was added. After an hour at 105°C analysis showed 98.6% DETEG, 1.4% METEG. After 3 ½ hours, analysis showed 99.25% DETEG, 0.75% METEG, and after five hours analysis showed 99.5% DETEG, 0.5% METEG.

Two liters of water was added to the mixture to dissolve the NaCl. After stirring overnight, the mixture separated into two layers. The aqueous lower layer contained 5.3% caustic while the upper organic layer was essentially free of caustic. This 5.3% caustic number represents 116.6 g. of NaOH recovered.

It is noted in the above that the total amount of caustic employed in the total reaction was 25% excess over theoretical less the recovered NaOH, leaving a net of 15% NaOH excess of caustic. A 29% by weight excess over theoretical of ethyl chloride was used in the reaction. It is believed that more adequate stirring could bring the ratio of caustic utilized closer to theoretical.

In subsequent runs the time required to increase the percentage of DETEG from 96% to 99.5% of DETEG product was decreased by raising the temperature in the supplemental reaction from about 105°C to 125°C while continuously using a Diens-Stark trap.

In subsequent runs an inert atmosphere was utilized to safeguard against side effects of oxygen such as a blanket of nitrogen or a gas selected from Group 0 of the Periodic Chart such as helium, neon, argon, etc.

EXAMPLE 3

Following the procedure in Example 2, tetraethylene glycol was charged into a reactor under an inert atmosphere of nitrogen and heated to 100°–105°C. In both the main reaction and supplemental reaction disclosed therein, the reactants, flake sodium hydorixde and ethyl chloride liquid, were added continuously rather than incrementally, and the pressure was kept at not exceeding 50 psig. Theoretical amounts of glycol, sodium hydroxide caustic, and ethyl chloride were utilized in the main reaction. After 4 hours the reaction vessel was cooled to less than 50°C, vented, and supplemental caustic and supplemental ethyl chloride (both about 15% of theoretical) were added to effect removal of water from the organic phase. Azeotropic distillation assisted also in the removal of water and in a supplemental reaction about 10% of the theoretical amount of caustic was added together with an equivalent amount of ethyl chloride. The mixture was heated at 105°C and subsequently at 125°–135°C until the reaction mix showed 99% DETEG and 1% METEG.

EXAMPLE 4

15 moles of tetraethylene glycol was charged into a reactor under a nitrogen blanket atmosphere and heated to 125°–130°C. 30 moles each of sodium hydroxide flakes and ethyl chloride liquid were added continuously to the reactor over a period of 3 hours. The reactant was not under pressure and was fitted with a cold finger to assist in water condensation. At the end of three hours, the reaction mixture obtained using theoretical reactant quantities was approximately 70% DETEG and 30% METEG. The excess ethyl chloride was distilled off after heated at 130°C and recycled. About 2/3 of the water formation present was removed by heating at 130°–140°C and purging with nitrogen over a period of less than one hour.

Then in a supplemental reaction in the same vessel and also fitted with a cold finger, caustic (NaOH flakes) in 25% of the theoretical amount and an equivalent amount of ethyl chloride were added to the reactor at 130°C. The reaction mix was stirred vigorously and heated at 130°–135°C for about 5 hours. At the present time analysis showed 99% DETEG and 1% METEG.

I claim:

1. In a modified Williamson process for the production of diethers from polyalkylene glycols using sodium hydroxide and a lower alkyl halide as reactants both in molar amounts ranging from 100–120% of theoretical values at a temperature of 100°–130°C and a pressure from atmospheric to about 50 psig in a main reaction and separating out the aqueous layer of sodium chloride, the improvement which comprises increasing the yield of the diether product from about 70% to at least 95% by then adding after said separation of the aqueous layer of sodium chloride an additional quantity of said sodium hydroxide and said alkyl halide each in the amount of about 20 –25% of theoretical and concurrently removing water of formation in a supplemental reaction which is carried out at a temperature of 105°–135°C and at a pressure from atmospheric to about 50 psig.

2. The method according to claim 1 wherein the water of formation is removed by cold condensation.

3. The method according to claim 1 wherein the water of formation is removed by azeotropic distillation utilizing a binary azeotrope including a benzene-toluene-xylene solvent as the organic fraction.

4. The method according to claim 3 wherein the azeotropic distillation utilizes a binary system of toluene/water.

5. The method according to claim 1 wherein the polyalkylene glycol is tetraethylene glycol and the alkyl halide is ethyl chloride.

6. The method according to claim 1 wherein the process is carried out in an inert atmosphere.

* * * * *